US010126201B2

(12) United States Patent
Van Wittenberghe et al.

(10) Patent No.: US 10,126,201 B2
(45) Date of Patent: Nov. 13, 2018

(54) FATIGUE TESTING OF A TEST SPECIMEN

(71) Applicant: ONDERZOEKSCENTRUM VOOR AANWENDING VAN STAAL N.V., Zelzate (BE)

(72) Inventors: Jeroen Stijn Juliaan Van Wittenberghe, Zelzate (BE); Philippe Octave Thibaux, Zelzate (BE)

(73) Assignee: ONDERZOEKSCENTRUM VOOR AANWENDING VAN STAAL N.V., Zelzate (BE)

( * ) Notice: Subject to any disclaimer, the term of this patent is extended or adjusted under 35 U.S.C. 154(b) by 149 days.

(21) Appl. No.: 14/782,083

(22) PCT Filed: Apr. 1, 2014

(86) PCT No.: PCT/EP2014/056535
§ 371 (c)(1),
(2) Date: Oct. 2, 2015

(87) PCT Pub. No.: WO2014/161858
PCT Pub. Date: Oct. 9, 2014

(65) Prior Publication Data
US 2016/0061688 A1    Mar. 3, 2016

(30) Foreign Application Priority Data
Apr. 3, 2013  (NL) .................................... 2010556

(51) Int. Cl.
G01M 7/02       (2006.01)
G01M 5/00       (2006.01)
(Continued)

(52) U.S. Cl.
CPC .......... G01M 7/025 (2013.01); G01M 3/2853 (2013.01); G01M 5/0025 (2013.01);
(Continued)

(58) Field of Classification Search
CPC ............. G01M 3/2853; G01M 5/0025; G01M 5/0033; G01M 5/0041; G01M 5/0058;
(Continued)

(56) References Cited

U.S. PATENT DOCUMENTS 3,290,926 A * 12/1966 Montano .................. G01N 3/32
                                                        73/577
4,475,399 A * 10/1984 Livingston ............. G01N 29/26
                                                        73/622
(Continued)

OTHER PUBLICATIONS

International Search Report and Written Opinon—PCT/EP2014/056535—dated Jul. 7, 2014.
(Continued)

Primary Examiner — J M Saint Surin
(74) Attorney, Agent, or Firm — Banner & Witcoff, Ltd.

(57) ABSTRACT

The invention pertains to a combination of a test rig and test specimen for performing a fatigue test, wherein the test specimen is non-axisymmetric and comprises:—a central element,—a first branch element, which has a longitudinal axis that extends at an angle to the longitudinal axis of the central element,—a joint connecting the first branch element to the central element, which has an in plane bending resonance frequency with an associated in plane bending mode shape, and an out of plane bending resonance frequency with an associated out of plane bending mode shape, wherein the in plane bending resonance frequency and the out of plane bending frequency are substantially the same, wherein the first node of the in plane bending mode shape and the first node of the out of plane bending mode shape are substantially at the same position at the first branch element and wherein the test rig comprises:—a support for supporting the test specimen,—an excitator for subjecting the test specimen to forced vibration at an excitation frequency.

23 Claims, 8 Drawing Sheets

Figure 4:
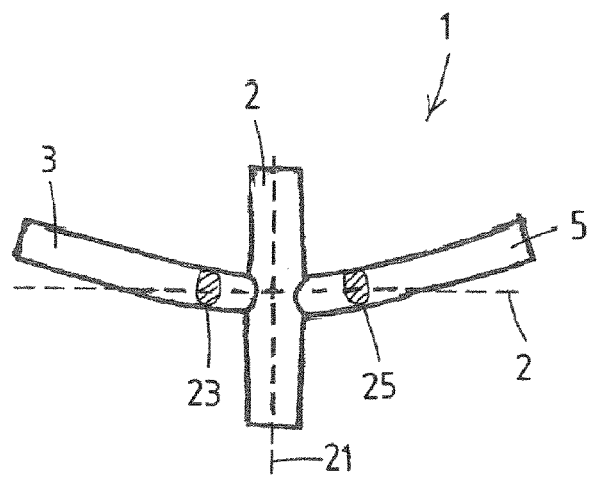

(51) Int. Cl.
*G01M 3/28* (2006.01)
*G01N 3/32* (2006.01)

(52) U.S. Cl.
CPC ........ *G01M 5/0033* (2013.01); *G01M 5/0041* (2013.01); *G01M 5/0058* (2013.01); *G01M 5/0066* (2013.01); *G01M 7/022* (2013.01); *G01N 3/32* (2013.01)

(58) Field of Classification Search
CPC .... G01M 5/0066; G01M 7/022; G01M 7/025; G01N 3/32
USPC .......................................................... 73/577
See application file for complete search history.

(56) References Cited

U.S. PATENT DOCUMENTS

| | | | | |
|---|---|---|---|---|
| 7,574,904 | B1* | 8/2009 | Davies | G01M 15/14 73/112.01 |
| 8,281,649 | B1* | 10/2012 | Crutchfield | G01M 15/14 73/112.01 |
| 8,573,038 | B1* | 11/2013 | Crutchfield | G01M 15/14 73/112.01 |
| 8,863,585 | B2* | 10/2014 | Wang | G01N 3/34 73/812 |
| 2009/0133381 | A1* | 5/2009 | Holmes | G01M 15/14 60/204 |
| 2010/0263448 | A1 | 10/2010 | Hughes et al. | |
| 2011/0041617 | A1 | 2/2011 | Cotrell et al. | |
| 2011/0041627 | A1* | 2/2011 | Gerlach | G01N 3/02 73/866 |
| 2014/0026674 | A1* | 1/2014 | Lund | G01M 13/04 73/800 |
| 2014/0202251 | A1* | 7/2014 | Murtas | G01M 5/0016 73/657 |

OTHER PUBLICATIONS

Dutch Search Report—NL Application 2010556—dated Jan. 16, 2014.
International Preliminary Report on Patentability—PCT/EP2014/056535—dated Jul. 10, 2015.
Tartibu et al. "Vibration Analysis of a Variable Length Blade Wind Turbine"—International Journal of Advances in Engineering & Technology, vol. 4, Issue 1—dated Jul. 2012.
Journal of Offshore Mechanics and Arctic Engineering: "Resonant Bending Fatigue Test Setup for Pipes With Optical Displacement Measuring System" (Aug. 2012, vol. 134).

* cited by examiner

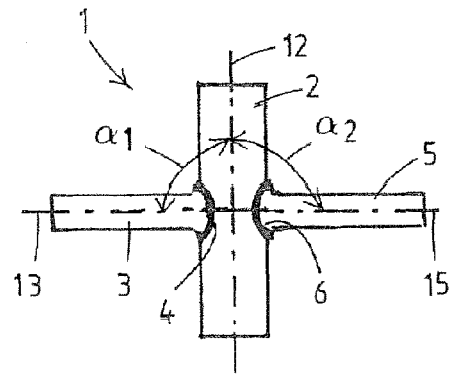
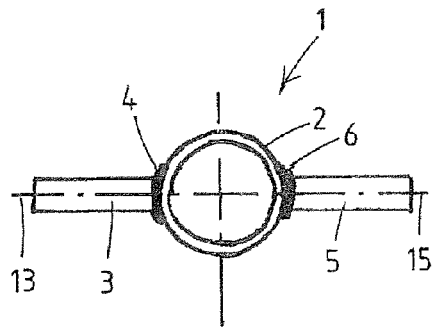
Fig.1a      Fig.1b
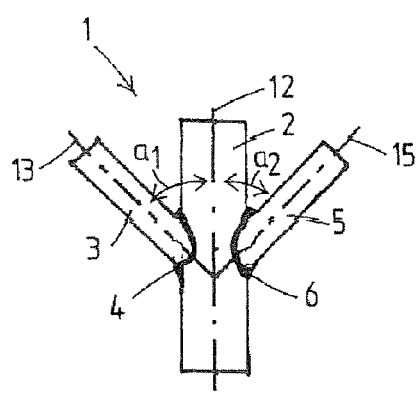
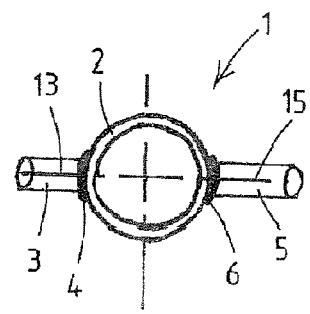
Fig.2a      Fig.2b
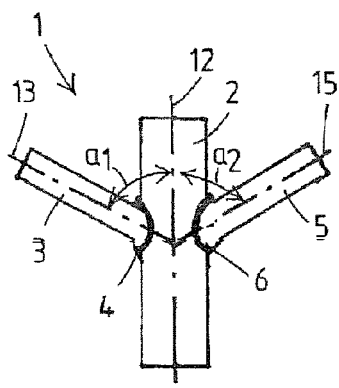
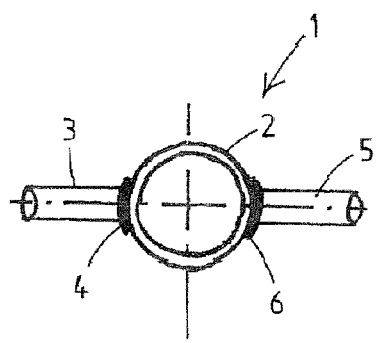
Fig.3a      Fig.3b

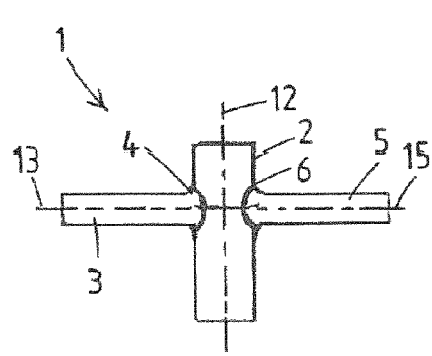
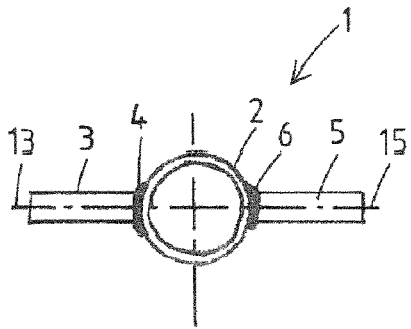
Fig.8a    Fig.8b
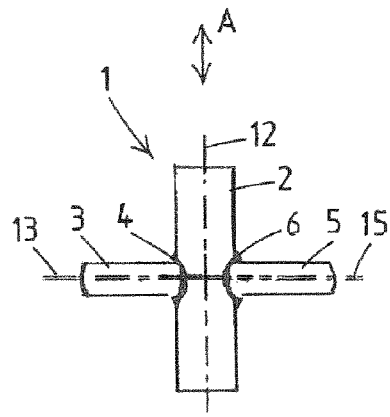
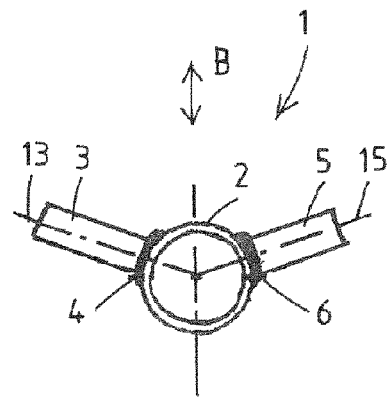
Fig.9a    Fig.9b
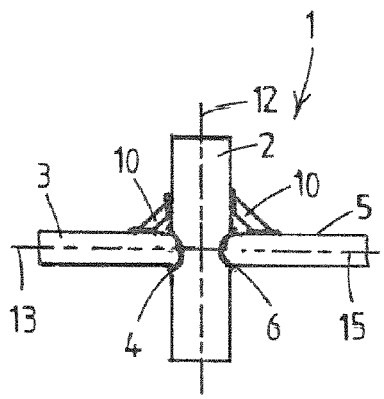
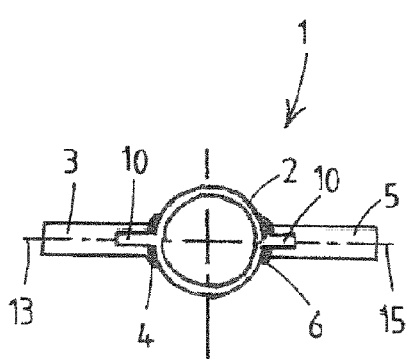
Fig.10a    Fig.10b

FATIGUE TESTING OF A TEST SPECIMEN

CROSS-REFERENCE TO RELATED APPLICATIONS

This application is a U.S. National Stage application under 35 U.S.C. § 371 of International Application PCT/EP2014/056535 (published as WO 2014/161858 A1), filed Apr. 1, 2014, which claims priority to Application NL 2010556, filed Apr. 3, 2013. Benefit of the filing date of each of these prior applications is hereby claimed. Each of these prior applications is hereby incorporated by reference in its entirety.

The invention pertains to fatigue testing of a test specimen.

In structures that are subjected to varying mechanical loads, damage may occur due to fatigue cracking. Already in the design stage of a structure, the resistance of the structure to fatigue cracking has to be evaluated so that the design can be optimized. However, in practice it is hard to obtain reliable data for evaluating the resistance to fatigue of a structure, in particular when welds or other types of joints are present.

Welds behave different from undisturbed base material. The fatigue strength of welds depends on several parameters, like the geometry of the weld, the welding process that has been applied, the base material and filler material that has been used and the type and direction of the mechanical loads that the weld will be subjected to.

In evaluating the resistance of a structure to fatigue, it is common practice to first calculate the expected levels of mechanical stress in the structure. These calculated levels of mechanical stress are then compared to so-called S-N-curves, which show the relationship between the level of mechanical stress and the number of load cycles before failure. S-N-curves are available for typical standard situations, but these standard situations very often differ significantly from the actual situation in the structure, for example because in the actual situation thick walled elements are used that have a different material behavior than thin walled elements. Therefore, the life span of a structure is hard to predict in a reliable way, and often significant safety factors are applied in the calculations. This however may lead to structures that are unnecessarily heavy and/or expensive.

In order to be able to make a better prediction of the expected life span of a structure, fatigue tests can be carried out. Often, fatigue tests are carried out on the actual structure (e.g. the blade of a wind turbine). In particular when large structures are to be tested, this is complicated and impractical. Large objects have to be handled and large alternating forces have to be applied, leading to large test rigs and high energy consumption.

In the Journal of Offshore Mechanics and Arctic Engineering of Aug. 2012, Vol. 134, an article was published having the title "Resonant Bending Fatigue Test Setup for Pipes With Optical Displacement Measuring System." This article describes the testing of a test specimen that is made up out of two pipes, which pipes are arranged with their longitudinal axes in line with each other, an end of one pipe being connected to an end of the other pipe. The connection between the pipes could be a weld (e.g. a girth weld) or a threaded connection. This results in the test specimen being a long pipe with a weld or threaded connection in the middle.

This known test specimen is arranged on supports, and a drive with an eccentric weight is connected to one of the free ends of the test specimen. The eccentric weight is rotated, which causes imbalance forces that are exerted on the test specimen at an excitation frequency, thus causing forced vibration of the test specimen. The excitation frequency is chosen such that it is close to a natural frequency that has an associated mode shape in the form of a standing wave that rotates at the excitation frequency. So, the standing wave induces rotational bending of the test specimen. The supports of the test rig are arranged such that they support the test specimen in the nodes of the standing wave.

This particular mode shape occurs due to the test specimen having an axisymmetric shape.

This known way of fatigue testing is not suitable for obtaining data that is suitable for determining the life span of joints between structural elements that are non-coaxial, that is, joints between two structural elements that are at a relative angle other than 0° or 180°. For example, the weld geometry and the welding processes that are used to connect non-coaxial structural elements to each other are too different from what is used to connect coaxial structural elements. Also the mechanical loads on joints between structural elements that are non-coaxial and joints between coaxial structural elements are too different, e.g. because these mechanical loads act in a different direction.

Furthermore, it is known from the art to subject wind turbine blades to bi-axial resonant bending fatigue tests. This is for example described in US2011/0041617 and US2010/0263448. However, wind turbine blades are essentially cylindrical in shape and as such do not contain as part of their own structure an element that extends at a relative angle other than 0° or 180° from their longitudinal direction. Sometimes, parts of the test rig are arranged onto the wind turbine to be tested, for example to invoke excitation of the wind turbine blade to be tested. Such parts of the test rig may extend at a relative angle other than 0° or 180° from the longitudinal direction of the wind turbine blade, but they do not form part of test specimen as the connection of these parts of the test rig to the wind turbine blades are not connections to be tested in the fatigue test of the wind turbine blade.

The wind turbine blades that are used as test specimens in US2011/0041617 and US2010/0263448 do not contain a structural element that extends at a relative angle other than 0° or 180° from their longitudinal direction nor a joint to such a structural element. Therefore, the known way of fatigue testing as described in US2011/0041617 and US2010/0263448 is also not suitable for obtaining data that is suitable for determining the life span of joints between structural elements that are non-coaxial, that is, joints between two structural elements that are at a relative angle other than 0° or 180°.

It is the object of the invention to provide a suitable way of performing fatigue tests on a test specimen, and to provide a combination of a test rig and test specimen to do so.

This object is achieved with the combination of a test rig and test specimen according to claim 1 and with the method according to claim 15.

In accordance with the invention, a combination of a test rig and test specimen is provided for performing a fatigue test of said test specimen, wherein the test specimen is non-axisymmetric and comprises:
  a central element, said central element having a longitudinal axis,
  a first branch element, said first branch element having a longitudinal axis that extends at an angle to the longitudinal axis of the central element, a joint connecting the first branch element to the central element, wherein the non-axisymmetric test specimen has a plurality of resonance frequencies with associated mode shapes, which plurality of resonance frequencies comprises an in plane bending resonance frequency with an associated in plane bending mode shape, and an out of plane bending resonance frequency with an associated out of plane bending mode shape, wherein the in plane bending resonance frequency and the out of plane bending frequency are substantially the same, and wherein the in plane bending mode shape comprises a first node, which first node is located at the first branch element, and wherein the out of plane bending mode shape comprises a first node, which first node is located at the first branch element, wherein the first node of the in plane bending mode shape and the first node of the out of plane bending mode shape are substantially at the same position at the first branch element, and wherein the test rig comprises:

a first support for supporting the test specimen, which first support supports the test specimen at or adjacent to the node of the in plane bending mode shape and the out of plane bending mode shape, an excitator for subjecting the test specimen to forced vibration at an excitation frequency.

The test specimen according to the invention has a non-axisymmetric shape. This allows to test joints that connect elements that extend under an angle other than 0° or 180° relative to each other. Many structures that are subjected to varying loads, e.g. jackets for wind turbines or oil and gas platforms, rely on these kinds of joints for their structural integrity.

The test specimen according to the invention is preferably made of metal. The metal can for example be steel. The steel can be coated or non-coated and/or painted or unpainted. As an alternative, the test specimen can be made of plastic. This plastic can for example be resin or a thermoplastic plastic. The resin of thermoplastic material is optionally provided with fibers, e.g. for reinforcement. Those fibers can be for example glass fibers or carbon fibers.

The test specimen comprises a central element. This central element has a longitudinal axis. The test specimen further comprises a first branch element. This first branch element has a longitudinal axis that extends at an angle other than 0° or 180° to the longitudinal axis of the central element. A joint connects the first branch element to the central element. This joint will in general be the part of the test specimen that the fatigue test focuses on.

Optionally, the test specimen is provided with a second branch element.

The presence of the first branch element and optionally a second branch element makes that the test specimen is not only non-axisymmetric, but also non-cylindrical.

The joint between the first branch element and the central element and/or the joint between the second branch element and the central element can take many forms. It can be for example a weld or a threaded connection or a flange connection or a part of a cast structural element or a glued connection. In case of a flange connection, the flanges can be connected by bolts and nuts or in any other suitable way, for example by a weld or by glue.

The test specimen is the structure that is to be tested by the fatigue test. The test specimen should or may fail during the fatigue test, depending on the set up of the fatigue test. The test rig applies the fatigue load onto the test specimen and supports the test specimen during the fatigue test. The test rig should remain intact during the fatigue test. The fatigue test should be designed, e.g. in terms of excitation frequency and expected mechanical loads on the test rig, to ensure this.

In accordance with the invention, the central element, the branch element and the joint between the central element and the branch element all form part of the test specimen. Optionally, an interface is present between the test specimen and the test rig, for example in order to physically impose the fatigue load onto the test specimen. Such an interface is not part of the test specimen and does not contain the branch element and/or joint in accordance with the invention, as the interface and the connection of the interface to the test specimen are not the parts to be tested in the fatigue test. The interface and the connection of the interface to the test specimen should remain intact during the fatigue test, while the test specimen should or may fail during the fatigue test.

The test specimen according to the invention does not necessarily be of the same dimensions as the actual structure for which the fatigue resistance has to be determined. The test specimen according to the invention can be a model for the actual structure. So, the invention is not limited to full size fatigue testing of the actual structure to be evaluated or a copy thereof.

As any structural object, the test specimen has a plurality of resonance frequencies with associated mode shapes. These include rigid body modes and mode shapes that cause deformation of the test specimen. Among the mode shapes that cause deformation of the test specimen, two mode shapes are of particular interest in view of the invention.

One of these two interesting mode shapes is what is called the "out of plane bending mode shape". This is the mode shape in which the test specimen deforms in such a way that the first branch element deflects out of the plane that is defined by the longitudinal axis of the central element and the longitudinal axis of the first branch element.

The other interesting mode shape is what is called the "in plane bending mode shape". In this mode shape, the first branch element deflects in this plane that is defined by the longitudinal axis of the central element and the longitudinal axis of the first branch element, in such a way that the central element moves in the direction of its longitudinal axis.

It was found that in test specimens having a certain geometry, the resonance frequencies and also the location of the nodes of these mode shapes are substantially the same.

This is most prominent in a test specimen that comprises a tubular central element, a tubular first branch element and a tubular second branch element. The longitudinal axes of the central element, the first branch element and the second branch element are all in the same plane and the two branch elements are connected to the central element at the same level, that is: at the same distance from the top end or bottom end of the central element, preferably halfway the central element. The angle between the longitudinal axis of the central element and the longitudinal axis of each branch element is between about 45° and about 135°, and preferably this angle is the same for both branch elements. Optionally, the angle between the longitudinal axis of the central element and the longitudinal axis of each branch element is between about 30° and about 150°, and preferably this angle is the same for both branch elements.

However, the desired resonance frequencies and the desired locations of the nodes of the mode shapes can also be achieved with test specimens that have a geometry that is a variant of this particular geometry, e.g. test specimens having just one branch element, or the first branch element being connected to the central element at a different level from the second branch element, or two branch elements extending not in the same plane. With these kinds of geometries, generally the weight distribution within the test specimen will have to be optimized in order to create the desired proximity of the resonance frequencies and optionally the desired location of the nodes. This can for example be achieved by providing additional test weights at strategic locations of the test specimen, and/or by filling at least a part of the test specimen with a liquid such as water, and/or by locally varying the wall thickness of a branch element and/or the central element. In case two or more branch elements are used, the geometry of different branch elements (e.g. length, diameter, wall thickness) can be different. It is possible that the weight distribution could be non-symmetrical in order to obtain the desired resonance frequencies and/or mode shapes. For example, it could be that an additional test weight has to be added to both the first and the second branch element, but that the size of the additional test weight on the first branch element is different from the additional test weight that has to be added to the second branch element, and/or that the additional test weight on the first branch element would have to be arranged closer to the central element than the additional test weight on the second branch element. Alternatively or in addition, it is possible to arrange one or more additional test weights non-coaxial with a branch element, for example by arranging it such that it is not axisymmetric relative to the longitudinal axis of a branch element. This can be done for example by arranging an additional test weight on the top or to the front of the branch element, and not arranging a further additional test weight diametrically opposite to it.

In a different approach however, instead of or in addition to the change in weight distribution to obtain the desired resonance frequencies and the desired locations of the nodes of the mode shapes, stiffeners, for example stiffener plates, are attached to the branch element or branch elements. Optionally, the stiffener is attached to the branch element or central element by welding.

Such a stiffener can extend between a branch element and the central element, but in addition or as an alternative, an individual stiffener is attached to a single branch element only, or to the central element only. In embodiments in which two or more branch elements are present, it is possible that each branch element is provided with its own stiffener or stiffeners.

The stiffeners change the stiffness in one or more directions of the branch element or central element to which they are attached. The stiffener can be for example arranged such that the stiffness of the test specimen in the direction that is relevant for the in plane bending modus is increased, but that the stiffness of the test specimen in the direction that is relevant for the out of plane bending modus is not or hardly changed. Of course, it is also possible that the stiffener is arranged such that the stiffness of the test specimen in the direction that is relevant for the out of plane bending modus is increased, but that the stiffness of the test specimen in the direction that is relevant for the in plane bending modus is not or hardly changed. The use of such stiffener allows to selectively change the resonance behaviour of the test specimen in the different bending modes.

In a possible embodiment, a stiffener is attached to a branch element between area in which the branch element is engaged by the support of the test rig and the joint that connects said branch element and the central element.

In a possible embodiment, multiple stiffeners are provided on a branch element or on each branch element and/or on the central element.

In a possible embodiment, the stiffener is a stiffener plate which is attached to a branch element in the longitudinal direction of said branch element.

In a possible embodiment, at least one stiffener is a stiffener plate, which stiffener plate extends in the longitudinal direction of the branch element to which it is connected, and in the plane of the out of plane bending mode shape or in the plane of the in plane bending mode shape.

In the test specimen, stress concentration factors are associated with the joint. These stress concentration factors are different at different locations within the joint, depending for example on the relative diameters and thicknesses of the central and branch elements, but also on the direction of the mechanical loads that are applied to the test specimen. This means that the stress levels will be different in the joint at the locations which are sensitive to the in plane bending mode than at the locations which are sensitive to the out of plane bending mode, even if the same mechanical loads are applied. The direction of the deformation due to the resonance of the in plane bending mode relative to the plane in which the stiffener extends is different from the direction of the deformation due to the resonance of the out of plane bending mode relative to the plane in which the stiffener extends, and with the different stress concentration factors, they cause different stress amplitudes in the joint in these different directions.

In a possible embodiment, the testing frequency is selected closer to the resonance frequency of bending mode that is associated with the lowest stress concentration at the joint than to the resonance frequency of bending mode that is associated with the highest stress concentration at the joint. This makes that the test specimen, and in particular the joint or joints between the central element and a branch element, still receives the desired level of mechanical stresses in the bending mode that is associated with the lowest stress concentrations.

Changing the weight distribution or applying stiffeners on one or more branch elements and/or the central element can also applied in test specimens in which the resonance frequencies and the locations of the nodes of the mode shapes are already substantially the same. It those cases, changing the weight distribution or applying stiffeners on one or more branch elements and/or the central element can be applied in order to shift the resonance frequencies towards a desired value (e.g. within the range that the excitator can apply) or to shift the position of the nodes to a desired location.

"Substantially the same resonance frequencies" should be understood as that in case the excitation frequency is chosen close to the two resonance frequencies, both mode shapes are excited without having to apply large amounts of energy in order to obtain enough deformation and mechanical stress in the joint to perform the fatigue test. It was found that if the lowest of the in plane bending resonance frequency and the out of plane bending resonance frequency is about 80% or more of the highest of the in plane bending resonance frequency and the out of plane bending resonance frequency, this already produces the effect according to the invention. Preferably, the lowest of the in plane bending resonance frequency and the out of plane bending resonance frequency is about 85% or more of the highest of the in plane bending resonance frequency and the out of plane bending resonance frequency. More preferably, the lowest of the in plane bending resonance frequency and the out of plane bending resonance frequency is about 90% or more of the highest of the in plane bending resonance frequency and the out of plane bending resonance frequency.

So, when the lowest of the in plane bending resonance frequency and the out of plane bending resonance frequency is about 80% or more of the highest of the in plane bending resonance frequency and the out of plane bending resonance frequency, the in plane bending resonance frequency and the out of plane bending frequency are considered to the "substantially the same".

It should be noted that it is generally not desirable to use an excitation frequency that is exactly the same as one of the resonance frequencies. In case the test specimen is excited at exactly one of its resonance frequencies, the vibration levels could go out of control.

The advantage of choosing an excitation frequency close to the resonance frequency is that a relative small amount of energy is needed to create and sustain the vibration in the test specimen. In general, an excitation frequency within a range between about 90% of the lowest of the in plane bending resonance frequency and the out of plane bending resonance frequency to about 110% of the highest of the in plane bending resonance frequency and the out of plane bending resonance frequency produces good results. Having an excitation frequency within a range between about 80% the lowest of the in plane bending resonance frequency and the out of plane bending resonance frequency to about 120% of the highest of the in plane bending resonance frequency and the out of plane bending resonance frequency is generally acceptable. In the method to the invention the excitation frequency will generally be in the range from about 80% of the lowest of the in plane bending resonance frequency and the out of plane bending resonance frequency to about 120% of the highest of the in plane bending resonance frequency and the out of plane bending resonance frequency. It is not necessary that the excitation frequency is between the two resonance frequencies. In particular when the resonance frequencies are very close together, e.g. 2 Hz or less apart, it will often be more practical to use an excitation frequency that is below the lowest resonance frequency of the two or above the highest resonance frequency of the two.

In accordance with the invention, the first node of the in plane bending mode shape and the first node of the out of plane bending mode shape are substantially at the same position at the first branch element. The "first node" is a node of a mode shape that is located at the first branch element. In case the test specimen also has a second branch element, the second node of the in plane bending mode shape and the second node of the out of plane bending mode shape are substantially at the same position at the second branch element. The "second node" is a node of a mode shape that is located at the second branch element.

"Substantially the same position" of the nodes of the two mode shapes means that there is an area in each branch element where the deformation of the branch element is low when both the in plane bending mode shape and the out of plane bending mode shape are excited.

The deformation in this area is low enough to make it practical for the support or supports of the test rig to engage the test specimen in this particular area. When a support of the test rig engages the test specimen at or close to a node, the support does not have to absorb high deflections of the test specimen during the fatigue test. This also makes that the mechanical loads (force, energy) that have to be absorbed by the support during the fatigue test are relatively low. In practice, "the first node of the in plane bending mode shape and the first node of the out of plane bending mode shape are substantially at the same position at the first branch element" means that the distance from the node in the first branch element in the in plane bending mode shape to the node in the first branch element in the out of plane bending mode shape should be about equal to or less than the diameter of the first branch element. Likewise, if a second branch element is present, "the second node of the in plane bending mode shape and the second node of the out of plane bending mode shape are substantially at the same position at the second branch element" means that the distance from the node in the second branch element in the in plane bending mode shape to the node in the second branch element in the out of plane bending mode shape should be about equal to or less than the diameter of the second branch element.

In practice, the distance between the first node of the in plane bending mode shape and the first node of the out of plane bending mode shape will generally be 200 mm or less, preferably 100 mm or less.

It is advantageous if the other resonance frequencies of the test specimen are relatively far removed from the in plane bending resonance frequency and the out of plane bending frequency. Preferably, other resonance frequencies are at least 25% higher than the highest of the in plane bending resonance frequency and the out of plane bending resonance frequency or at least 25% lower than the lowest of the in plane bending resonance frequency and the out of plane bending resonance frequency. This way, mainly (or only) the in plane bending mode shape and the out of plane bending mode shape are excited by the excitator during the fatigue test.

Optionally, the test specimen has at least one cavity that can be filled with a liquid (e.g. water) or a gas (e.g. compressed air or helium). If a gas is used, it preferably is a compressed gas, so a gas under pressure. It is possible that the test specimen is entirely hollow, such that a single cavity is present on the inside that extends into the central element as well as into the first branch element and—if present—the second branch element. It is also possible that the test specimen comprises a cavity in the central element and a separate cavity in the first branch element, and if a second branch element is present, a further separate cavity in the second branch element.

The cavity or cavities can be used for several purposes. For example, filling the cavity or cavities with a substance that has mass, such as a liquid, can change the weight distribution over the test specimen. Therewith, it can help to adjust the resonance frequencies of the test specimen, bringing the in plane bending resonance frequency and the out of plane bending frequency closer together or generally lowering the resonance frequencies. It can also help to adjust the position of the nodes in the in plane bending mode shape and the out of plane bending mode shape, bringing them closer together if desired.

The cavity or cavities can alternatively or in addition be used for crack detection. If the joint or joints to be tested forms part of the cavity wall, and the cavity is filled e.g. with a liquid or a gas, a leak and a drop in pressure will occur once a crack has grown through the thickness of the material of the joint. For example, when the joint is a weld, it is likely that fatigue cracks will form in the weld before they form in the base material. In that case, it makes sense to have the weld form part of the wall of the cavity when the cavity is used for crack detection.

When the cavity or cavities are filled with a gas or liquid for the purpose of crack detection, it is advantageous to measure the pressure of the gas or liquid in the cavity, so that a pressure drop can be detected quickly. Optionally, the test specimen is equipped with one or more sensor supports to which for example a pressure sensor can be mounted.

In a possible embodiment, a negative pressure is applied at the cavity, so the pressure in the cavity is lower than the ambient pressure. If the joint or joints to be tested forms part of the cavity wall, and a negative pressure is applied in the cavity, a change in pressure will occur once a crack has grown through the thickness of the material of the joint. So, this embodiment also allows crack detection by measurement of the pressure that is present inside the cavity. Optionally, the test specimen is equipped with one or more sensor supports to which for example a pressure sensor can be mounted.

Another way of crack detection is monitoring changes in the mode shape of the test specimen during the test. As a crack will alter the stiffness of the test specimen, at least locally, the mode shape will change somewhat too. These are generally subtle changes, in particular when the crack is still small. However, it is possible to detect such changes by measuring local displacement, velocity and/or acceleration of the test specimen. Preferably, the local displacement, local velocity and/or local acceleration are measured at a plurality of locations on the test specimen. The local displacement, velocity and/or acceleration can be measured e.g. by arranging sensors on the test specimen (optionally, the test specimen is provided with supports to do so), or contactless, e.g. in an optical way.

Another way of crack detection would be to use strain gauges, as the formation of a crack leads to local stress release near the crack.

Further ways of crack detection are for example penetrant dye testing, eddy current testing, ultrasonic testing or X-ray imaging. However, methods like these generally require that the fatigue test is interrupted or stopped in order for the crack testing to be carried out.

The excitator of the test rig applies a varying mechanical load to the test specimen at an excitation frequency, therewith subjecting the test specimen to forced vibration at this excitation frequency.

A suitable way of doing this involves the use of a rotatable eccentric weight in the excitator. The rotatable eccentric weight causes imbalance forces, which can be applied to the test specimen in order to obtain forced vibration of the test specimen. The imbalance forces can be used to alternatingly excite the in plane bending mode and the out of plane bending mode.

In a possible embodiment, a rotatable eccentric weight is connected to a branch element of the test specimen, for example at the free end of the branch element, so at the end of the branch element that is not connected to the central element. The rotatable eccentric weight is rotatable relative to the branch element; the branch element is not rotated. In such an embodiment, the eccentric weight can be coupled to an electric motor by means of a cardan shaft. By selecting a rotational speed of the electric motor, the excitation frequency can be set. Preferably, if an electric motor is used to drive the excitator, the electric motor is provided with a motor control system that allows to accurately control, set and/or adjust the rotational speed of the motor.

In general, preferably the excitator is adjustable, allowing the excitation frequency to be set at a desired value.

In general, optionally the in plane bending mode shape and the out of plane bending mode shape are excited in an alternating way by the excitator.

In practical cases, the excitation frequency that is used with the fatigue test in accordance to the invention could be between 10 Hz and 60 Hz, for example. This is different from e.g. fatigue testing of wind turbine blades, where typically excitation frequencies below 5 Hz are used.

The test rig comprises at least a first support for supporting the test specimen. When the test specimen is arranged in or on the test rig, the test specimen is arranged such that the first support of the test rig supports the test specimen at or adjacent to the node of the in plane bending mode shape and the out of plane bending mode shape. This way, the test rig will not be subjected to large dynamic forces.

In a possible embodiment, the test rig is provided with a second support. In such an embodiment, the first support of the test rig can engage the first branch element and the second support can engage the second branch element.

Optionally, at least the first support of the test rig is movable such that its position can be matched to the location of the first node of the in plane bending mode and/or the out of plane bending mode. Optionally, if also a second support is present in the test rig, the second support is movable too. This is however not necessary, because if just the first support is movable, it is still possible to support both branches of the test specimen at or close to the first and second nodes of the in plane bending mode and the out of plane bending mode, in particular if the excitator is flexible or movable too.

Optionally, the test specimen is tested in free floating conditions. However, also in such an embodiment, a strap or the like can be applied over the test specimen for safety reasons. Alternatively, although most likely far less common, the test specimen will be gripped by the supports of the test rig more tightly, such that no free floating conditions are present.

Optionally the test rig comprises safety provisions to prevent rotation of the test specimen. These safety provisions for example comprise a strap that is applied over the test specimen, for example at or close to the support or supports of the test rig.

The supports of the test rig are arranged on a base, for example a floor or a structure mounted on a floor. In case one or more supports are movable, they generally are movable relative to said base. The excitator will generally also be arranged on a base. This can be the same base as the one onto which the support or supports are arranged, but it can also be a different base. In that case, the base onto which the support or supports are arranged optionally is isolated with respect to vibration transfer from the base onto which the excitator is arranged.

The combination of the test rig and test specimen and the method for fatigue testing according to the invention can be used for a wide range of sizes of test specimens. It is also suitable for very large test specimens, e.g. test specimens having a central element with an outer diameter of 500 to 2000 mm and a wall thickness of 15 to 80 mm, and/or a branch element of 200 to 1000 mm and a wall thickness of 10 to 60 mm. Structural elements of such sizes are used e.g. in offshore jackets. The combination of the test rig and test specimen and the method for performing fatigue tests according to the invention is therefore suitable for evaluating the fatigue strength and/or expected life span of joints in this kind of structures.

It is possible that the test specimen according to the invention further comprises one or more stiffeners, shores or the like. Such a stiffener or shore could for example extend between the central element and the first branch element, and/or, if a second branch element is present, between the central element and the second branch element.

The invention further pertains to a method for performing a fatigue tests on a test specimen, which method comprises the following steps:
- providing a combination of a test rig and a test specimen according to the invention,
- arranging the test specimen in the test rig, such that the first support of the test rig supports the first branch element at or adjacent to the first node of both the in plane bending mode shape and the out of plane bending mode shape,
- subjecting the test specimen to forced vibration by the excitator at an excitation frequency that is close to the in plane bending resonance frequency and the out of plane bending resonance frequency, thereby exciting the in plane bending mode and the out of plane bending mode.

The invention further pertains to a method for designing a fatigue test of a test specimen, in which fatigue test a combination of a test rig and test structure according to the invention is used and which fatigue test is carried out as described above.

This method comprises the following steps:
- selecting a base geometry for the test specimen, including selecting the number of branch elements to be connected to the central element and the position and direction of these branch elements,
- selecting the shape of the central element and any branch elements,
- selecting the length and cross sectional sizes (e.g. the outer diameter and/or wall thickness) of the central element and any branch elements,
- calculating the in plane bending resonance frequency, the in plane bending mode shape, the out of plane bending resonance frequency, the out of plane bending mode shape and optionally any further resonance frequencies that might be close to the in plane bending resonance frequency and/or out of plane bending resonance frequency,
- determining the difference between the in plane bending resonance frequency and the out of plane bending resonance frequency,
- evaluating whether this difference between the in plane bending resonance frequency and the out of plane bending resonance frequency is small enough to each other to be able to apply the method for performing a fatigue test according to the invention,
- determining the difference in location of the node each branch element in the in plane bending mode shape and the location of this node in the out of plane bending mode shape,
- optionally evaluating whether this difference in location of the node each branch element in the in plane bending mode shape and the location of this node in the out of plane bending mode shape is small enough to each other to be able to apply the method for performing a fatigue test according to the invention,
- if the difference between the in plane bending resonance frequency and the out of plane bending resonance frequency or the optionally calculated difference in location of the node each branch element in the in plane bending mode shape and the location of this node in the out of plane bending mode shape is too large, adapting the weight distribution in the test specimen and/or the length and cross sectional sizes of the central element and any branch elements and/or adapting the stiffness of a branch element and/or the central element in at least one direction by attaching a stiffener to said branch element and/or central element in order to shift the location of the nodes and/or the resonance frequencies.

The invention further pertains to a test specimen for use in a combination of a test rig and a test specimen according to the invention or in the method according to the invention, wherein the test specimen is non-axisymmetric and comprises:
- a central element, said central element having a longitudinal axis,
- a first branch element, said first branch element being made of metal and having a longitudinal axis that extends at an angle to the longitudinal axis of the central element,
- a joint connecting the first branch element to the central element, wherein the non-axisymmetric test specimen has a plurality of resonance frequencies with associated mode shapes, which plurality of resonance frequencies comprises an in plane bending resonance frequency with an associated in plane bending mode shape, and an out of plane bending resonance frequency with an associated out of plane bending mode shape, wherein optionally the in plane bending mode shape comprises a first node, which first node is located at the first branch element, and wherein the out of plane bending mode shape comprises a first node, which first node is located at the first branch element, the first node of the in plane bending mode shape and the first node of the out of plane bending mode shape being substantially at the same position at the first branch element, and wherein the test specimen is further provided with at least one support for a sensor, and/or wherein the test specimen is provided with an additional test weight at the central element and/or at at least one branch element, wherein optionally the additional test weight is arranged non-coaxial with the branch element.

The invention will be described in more detail below under reference to the drawing, in which in a non-limiting manner exemplary embodiments of the invention will be shown.

Figure 5:
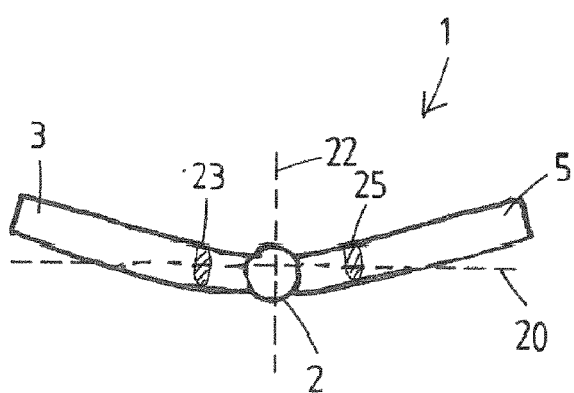
Figure 6:
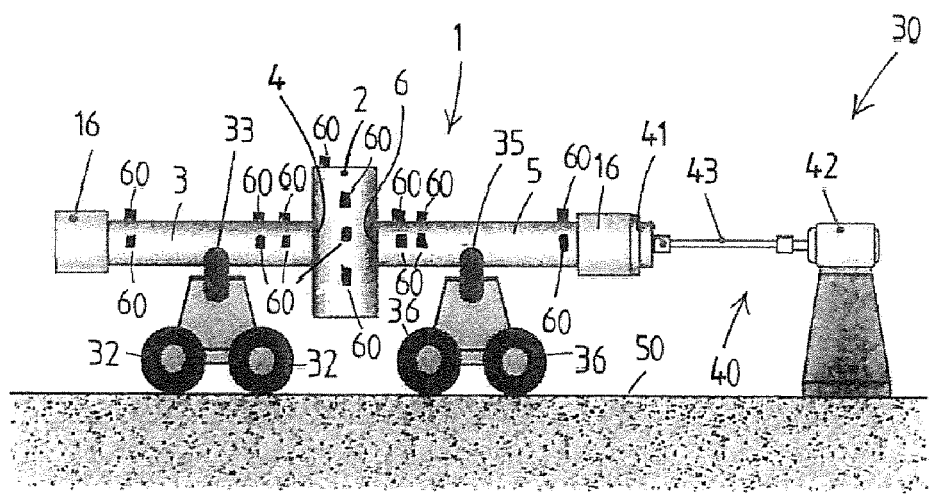
Figure 7:
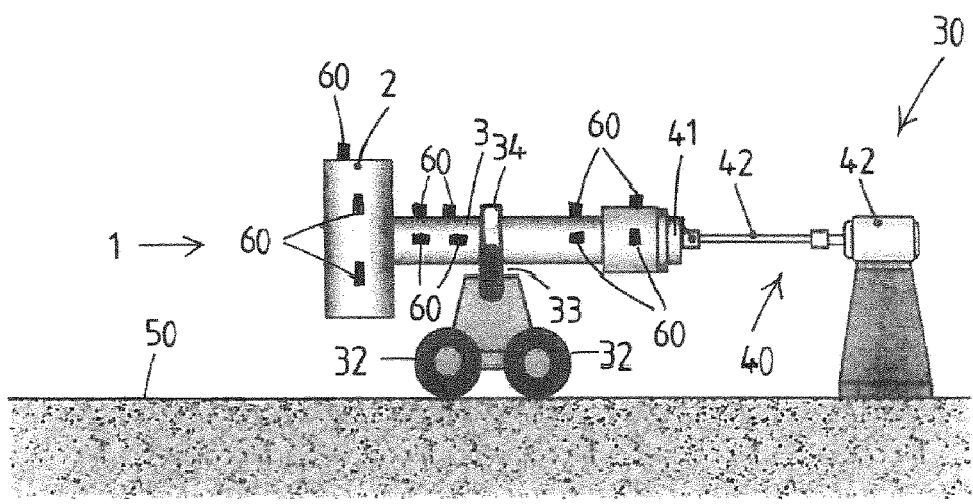
Figures 16A, 16B:
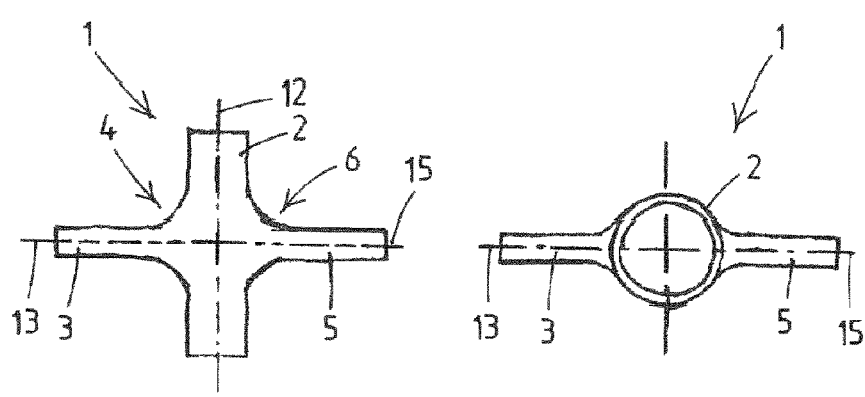
Figure 17:
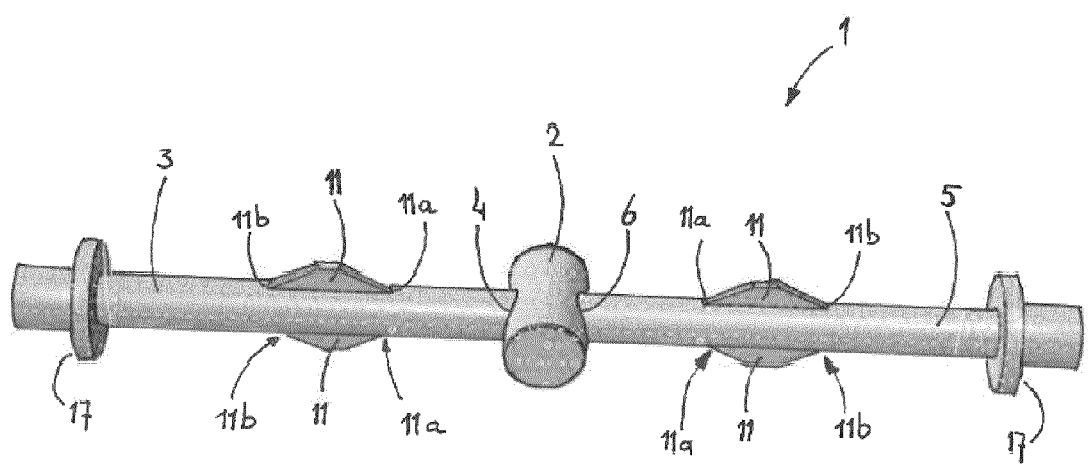

The drawing shows in:

FIG. 1*a:* a first example of a test specimen according to the invention, in front view, FIG. 1*b:* a first example of a test specimen according to the invention, in top view, FIG. 2*a:* a second example of a test specimen according to the invention, in front view, FIG. 2*b:* a second example of a test specimen according to the invention, in top view, FIG. 3*a:* a third example of a test specimen according to the invention, in front view, FIG. 3*b:* a third example of a test specimen according to the invention, in top view, FIG. 4: the in plane bending mode shape, illustrated in the test specimen according to FIG. 1, FIG. 5: the out of plane bending mode shape, illustrated in the test specimen according to FIG. 1, FIG. 6: a first example of a combination of a test rig and test specimen according to the invention, FIG. 7: a second example of a combination of a test rig and test specimen according to the invention, FIGS. 8*a*-8*b*, 9*a*-9*b*, 10*a*-10*b*, 11*a*-11*b*, 12*a*-12*b*, 13*a*-13*b*, 14*a*-14*b*, 15*a*-15*b*, 16*a*-16*b*: further examples of test specimens according to the invention, FIG. 17: a further example of a test specimen according to the invention.

FIG. 1a shows a first example of a test specimen 1 according to the invention, in front view. FIG. 1b shows the same test specimen 1 in top view.

The test specimen 1 comprises a central element 2. The central element 2 is made of metal. It has a longitudinal axis 12. The test specimen according to FIG. 1 further comprises a first branch element 3. The first branch element 3 is also made of metal and has a longitudinal axis 13. The test specimen according to FIG. 1 further comprises a second branch element 5. The second branch element 5 is also made of metal and has a longitudinal axis 15.

In the test specimen according to FIG. 1, a joint 4, for example a weld, connects the first branch element 3 to the central element 2. A joint 6, for example a weld, connects the second branch element 5 to the central element 2. The longitudinal axis 13 of the first branch element 3 is at a relative angle α1 to the longitudinal axis 12 of the central element 2.

The longitudinal axis 15 of the second branch element 5 is at a relative angle α2 to the longitudinal axis 12 of the central element 2. In the example of FIG. 1, both angle α1 and α2 are 90°.

As can be seen in FIG. 1a, the first branch element 3 and the second branch element 5 are connected to the central element 2 at the same level, that is: at the same distance from the top end or bottom end of the central element. In the example of FIG. 1, the branch elements 3,5 are connected to the central element 2 halfway the central element, so as far from the top end as from the bottom end of the central element 2.

As can be derived from FIG. 1a and FIG. 1b together, the longitudinal axis 12 of the central element 2, the longitudinal axis 13 of the first branch element 3 and the longitudinal axis 15 of the second branch element 5 all lie in the same plane. The first branch element 3 and the second branch element 5 are arranged on opposite sides of the central element 2 and they are coaxial with each other.

In the example of FIG. 1, the central element 2 and both branch elements 3,5 are tubular. In the test specimen 1 of FIG. 1, in plane bending resonance frequency and the out of plane bending resonance frequency are already close together, without the need for e.g. applying additional weights or locally varying the wall thickness of the central element and/or branch elements.

For example, if the central element 2 is 4 meters long, has an outer diameter of 900 mm and a wall thickness of 60 mm, and the distance from the center of the central element 2 to the free end of each of the branch elements is 4 meters, and the branch elements have an outer diameter of 600 mm and a wall thickness of 15 mm, then the out of plane bending resonance frequency is 37.9 Hz and the in plane bending frequency is 38.9 Hz. This is close enough to say that the out of plane bending resonance frequency and the in plane bending resonance frequency are substantially the same in the sense of this invention.

The next resonance frequency is 55.8 Hz, so that is more than 25% higher than the in plane bending resonance frequency (which is in this example higher than the out of plane bending resonance frequency). This is sufficiently far removed from the out of plane bending resonance frequency and the in plane bending resonance frequency. When the excitation frequency is selected close to the out of plane bending resonance frequency and the in plane bending resonance frequency, say at somewhere in the range from 35 Hz to 42 Hz, the in plane bending mode and the out of plane bending mode will be excited, but the next vibration mode (having the resonance frequency of 55.8 Hz) will not be excited.

The nodes of the in plane bending mode and the out of plane bending mode for this test specimen 1, with the dimensions given above, in each of the branch elements 3,5 are also already close together. In both mode shapes, the distance between the first and second node is about 2.12 m. The position of the first node in the in plane bending mode shape and the position of the first node in the out of plane bending mode shape is less than 0.01 m, which is negligible when seen in relation to the size of the test specimen. The same applies to the position of the second node in the in plane bending mode shape and the position of the second node in the out of plane bending mode shape. So, there is also no need to e.g. apply additional weights or locally vary the wall thickness of the central element and/or branch elements in order to move the nodes closer together.

FIG. 2a shows a second example of a test specimen 1 according to the invention, in front view. FIG. 2b shows the same test specimen 1 in top view.

The test specimen 1 of FIG. 2 is a variant of the test specimen 1 of FIG. 1. The geometry is the same, except that in the embodiment of the test specimen 1 of FIG. 2, the angle α1 (between the longitudinal axis 12 of the central element 2 and the longitudinal axis 13 of the first branch element 3) and α2 (between the longitudinal axis 12 of the central element 2 and the longitudinal axis 15 of the second branch element 5) are 45° instead of 90°.

FIG. 3a shows a third example of a test specimen 1 according to the invention, in front view. FIG. 3b shows the same test specimen 1 in top view.

The test specimen 1 of FIG. 3 is a variant of the test specimen 1 of FIG. 1 and of FIG. 2. The geometry is the same, except that in the embodiment of the test specimen 1 of FIG. 3, the angle α1 (between the longitudinal axis 12 of the central element 2 and the longitudinal axis 13 of the first branch element 3) and α2 (between the longitudinal axis 12 of the central element 2 and the longitudinal axis 15 of the second branch element 5) are 60° instead of 90° or 45°, respectively.

In the test specimens 1 of FIG. 2 and FIG. 3, the out of plane bending resonance frequency and the in plane bending resonance frequency are somewhat farther apart than in the test specimen 1 of FIG. 1. Also the nodes in the branch elements of the in plane bending mode and the out of plane bending mode will be a bit farther apart. Whether measures have to be taken to shift the out of plane bending resonance frequency and the in plane bending resonance frequency or the position of the nodes of the in plane bending mode and the out of plane bending mode closer together (e.g. by applying additional weights or locally varying the wall thickness of the central element and/or branch elements) will depend on the actual geometry of the test specimen 1.

For example, a test specimen 1 with the shape as shown in FIGS. 3a and 3b, and central element 2 being 4 meters long, having an outer diameter of 900 mm and a wall thickness of 60 mm, and the distance from the center of the central element 2 to the free end of each of the branch elements being 4 meters, and the branch elements having an outer diameter of 600 mm and a wall thickness of 15 mm, will still have the nodes of the in plane bending mode and the out of plane bending mode in each of the branch elements close enough together. Also, the out of plane bending resonance frequency and the in plane bending resonance frequency are still close enough together to regarded as "substantially the same" in the sense of the invention: 40.0 Hz for the in plane bending mode and 44.0 Hz for the out of plane bending mode.

The next resonance frequency is 57.6 Hz, so that is more than 25% above the out of plane bending resonance frequency (which in this example is higher than the in plane bending resonance frequency). This is sufficiently far removed from the out of plane bending resonance frequency and the in plane bending resonance frequency.

FIG. 4 shows the in plane bending mode shape, illustrated in the test specimen 1 according to FIG. 1.

Dashed line 21 in FIG. 4 indicates the direction of the longitudinal axis of the central element 2 when the test specimen 1 is not vibrating or subjected to a mechanical load. Dashed line 20 in FIG. 4 indicates the direction of the longitudinal axis of the branch elements 3,5 when the test specimen 1 is not vibrating or subjected to a mechanical load. The solid lines in FIG. 4 show the in plane bending mode shape of test specimen 1.

It can be seen that the central element 2 does not deform significantly compared to the branch elements 3,5 in this mode shape. It moves back and forth in the direction of its longitudinal axis. The branch elements 3,5 deflect in the plane that is defined by the longitudinal axis of the central element 2 and the longitudinal axes of the branch elements in their undeflected state.

The in plane bending mode shape has two nodes, one on the first branch element 3 and one on the second branch element 5. The first node, on the first branch element 3, is located in the hatched area 23 that is shown in FIG. 4. The second node, on the second branch element 5, is located in the hatched area 25 that is shown in FIG. 4.

FIG. 5 shows the out of plane bending mode shape, illustrated in the test specimen according to FIG. 1.

Dashed line 20 in FIG. 5 indicates the direction of the longitudinal axis of the branch elements 3,5 when the test specimen 1 is not vibrating or subjected to a mechanical load.

The solid lines in FIG. 5 show the out of plane bending mode shape of test specimen 1.

It can be seen that the central element 2 moves back and forth in the direction of dashed line 22. The branch elements 3,5 deflect out of the plane that is defined by the longitudinal axis of the central element 2 and the longitudinal axes of the branch elements in their undeflected state.

The out of plane bending mode shape has two nodes, one on the first branch element 3 and one on the second branch element 5. The first node, on the first branch element 3, is located in the hatched area 23 that is shown in FIG. 5. The second node, on the second branch element 5, is located in the hatched area 25 that is shown in FIG. 5.

When comparing FIG. 4 and FIG. 5, it can be seen that the first node, that is located on the first branch element 3, of the in plane bending mode shape is situated at substantially the same location on the first branch element 3 as the first node (located on the first branch element 3) in the out of plane bending mode shape. The same applies for the second node, that is located on the second branch element 5. The second node of the in plane bending mode shape is at substantially the same location on the second branch element 3 as the second node in the out of plane bending mode shape.

Therefore, according to the invention, during the test, the test specimen 1 will be supported at the branch elements 3,5, at or adjacent to the position indicated by the hatched areas 23, 25.

FIG. 6 shows a first example of a combination of a test rig 30 and test specimen 1 according to the invention.

In the example of FIG. 6, a test specimen 1 generally in accordance with FIG. 1 is shown. However, in the example of FIG. 6, this test specimen 1 has been provided with additional test weights 16 at the free end of each branch elements 3,5. The free end of a branch element 3,5 is the end that is not connected to the central element 2.

The additional test weights 16 can have the same mass, but alternatively they have a different mass. For example, the additional test weight 16 that is arranged at the free end of the first branch element 3 can be heavier than the additional test weight 16 that is arranged at the free end of the second branch element 5 in order to compensate for any additional weight that is present due to drive 41 which is connected to the free end of the second branch element 5 as well.

Instead of the test specimen 1 shown in the example of FIG. 6, test specimens 1 according to the invention that have a different geometry (e.g. the ones shown in FIG. 2, FIG. 3, FIG. 8, FIG. 9, FIG. 10) can be used in combination with the test rig 30 that is shown.

The test rig 30 that is shown in FIG. 6 is arranged on a base 50. This base is preferably flat, smooth and sturdy. In the example of FIG. 6 the base is a floor, for example a concrete floor, but alternatively the base can for example be a structure mounted on a floor. In advantageous embodiments of the test rig 30, measures have been taken to reduce the dynamic mechanical loads that are exerted on the base 50 as much as possible. However, the invention allows for testing of large and heavy test specimens. If such large and heavy test specimens are to be tested, the base will still need to be strong.

The test rig 30 of FIG. 6 comprises a first support 33 and a second support 35. The first support 33 supports the first branch element 3 and the second support 35 supports the second branch element 5. The first support 33 is arranged such that it engages the first branch element 3, preferably at or adjacent to the node in the first branch element 3 of the in plane bending mode shape and at or adjacent to the node in the first branch element 3 of the out of plane bending mode shape. The second support 35 is arranged such that it engages the second branch element 5, preferably at or adjacent to the node in the second branch element 5 of the in plane bending mode shape and at or adjacent to the node in the second branch element 5 of the out of plane bending mode shape.

In the example of FIG. 6, both the first and the second support 33,35 are movable relative to the base 50. In this example, the supports 33, 35 are provided with wheels 32,36. The wheels 32,36 are optionally provided with rubber tires, for reducing the impact of the vibrations of imposed on the test specimen 1 onto the test rig 30 and the base 50.

The test rig 30 further comprises an excitator 40. The excitator 40 in this example comprises a drive 41 and an electric motor 42, and are coupled by a cardan shaft 43.

The drive 41 comprises at least one rotatable eccentric weight. The electric motor 42 drives the rotation of the eccentric weight via the cardan shaft 42. The rotation of the eccentric weight of the drive 41 produces imbalance forces that subject the test specimen 1 to a forced vibration at an excitation frequency. In practical cases, the excitation frequency could be between 10 Hz and 60 Hz, for example.

The electric motor 42 is preferably provided with a motor control system, that allows to set and/or adjust the rotational speed of the motor 42, and therewith the excitation frequency of the excitator. Preferably, the motor control system is such that it allows an accurate control of the motor speed and therewith of the excitation frequency.

Due to the rotating nature of the imbalance forces, the in plane bending mode shape and the out of plane bending mode shape are excited in an alternating way.

The excitation frequency is set close to the in plane bending resonance frequency and the out of plane bending resonance frequency, so that both the in plane bending mode and the out of plane bending mode are excited by the imbalance forces.

In the example of FIG. 6, the test specimen 1 has been instrumented with a number of sensors 60. Optionally, the test specimen 1 is provided with a number of supports for holding these sensors 60. The sensors 60 are for example displacement transducers, velocity transducers or acceleration transducers. These transducers can be used for example to monitor any changes in mode shape that could be indicative for the presence of a fatigue crack. It is possible that as an alternative or in addition, a sensor 60 in the form of a pressure transducer is present.

The use of a pressure transducer is useful when the test specimen 1 comprises a cavity that is filled with e.g. a gas or a liquid. If one or both of the joints 4,6 form part of the wall of that cavity, and a fatigue crack appears that extends through the entire thickness of the joint, the pressure in the cavity will drop. The pressure transducer should be arranged such that it detects such a pressure drop. So, if a pressure drop is measured by this pressure transducer, this indicates that a crack has formed. In case the joints 4,6 are welds, they have a lower resistance to fatigue than the base material of the central element 2 and the branch elements 3,5, it is likely that this crack is present in one of the joints 4,6.

FIG. 7 shows a second example of a combination of a test rig 30 and test specimen 1 according to the invention.

The test rig 30 in this example is similar to the one shown in FIG. 6. It has been modified to be suitable for test specimens 1 that have a central element 2 and only one branch element 3. Therefore, the test rig 30 of FIG. 7 has only one support 33. This support 33 in the example of FIG. 7 is movable, so that it can be arranged in such a way that it engages the branch element 3 at or adjacent to the node in the first branch element 3 of the in plane bending mode shape and at or adjacent to the node in the first branch element 3 of the out of plane bending mode shape.

Optionally, the geometry of the test specimen is adjusted such that the center of gravity of the test specimen is close the nodes and/or close to the support 33. Optionally, further provisions are made to stabilize the test specimen during the test. These provisions could for example include springs or straps.

In the example of FIG. 7, a strap 34 is present to hold the test specimen 1 in place relative to the support 33. The strap 34 is merely a safety measure, as the support 33 engages the first branch element 3 at or adjacent to a node of both excited mode shapes. The strap 34 helps to prevent undesired rotation of the test specimen relative to the test rig.

Straps 34 can be used in the test rig 30 that is shown in FIG. 6 too.

The excitator 40 and the sensors 60 in the example of FIG. 7 are the same as in the example of FIG. 6.

FIGS. 8 to 16 show further examples of test specimens according to the invention.

FIG. 8 shows a variant of the test specimen 1 according to FIG. 1. FIG. 8a shows the test specimen 1 in front view, FIG. 8b shows the test specimen 1 in top view.

In the variant of FIG. 8, the first branch element 3 and second branch element 5 are not arranged halfway the central element 2. In his example, the branch elements 3,5 are arranged closer to the top of the central element 2. This makes that when the test specimen 1 is arranged in a test rig according to the invention, e.g. the test rig of FIG. 6, gravity will hold the test specimen 1 in place in a more stable way, with the longer, and therefore heavier, part of the central element pointing downwards. This reduces the risk of undesired rotation of the test specimen relative to the test rig.

Test specimens 1 of the types as shown in FIG. 2 and FIG. 3 can be modified likewise, as can the other test specimens according to the invention, such that they have their branch elements 3,5 not halfway the central element 2.

Another variant (not shown) is to arrange the branch elements 3,5 halfway the central element, but to add additional weight to the lower part of the central element 2, at the bottom end or between the bottom end and the middle of the central element 2. This can be done by adding additional test weights or by filling a cavity in the lower part of the central element with for example a liquid (e.g. water). This can be done in any of the test specimens shown in FIGS. 1-3 and 8-16.

FIG. 9 shows another variant of the test specimen 1 according to FIG. 1. FIG. 9a shows the test specimen 1 in front view, FIG. 9b shows the test specimen 1 in top view.

In the variant of FIG. 9, the first and second branch elements 3,5 extend under an angle relative to each other. This will cause a shift in the position of the nodes of the in plane bending mode shape and/or the out of plane bending mode shape, and probably also a shift in the in plane bending resonance frequency and the out of plane bending resonance frequency. This variant of the test specimen can be used for adapting the resonance frequencies and/or position of the nodes in case the rest of the geometry of the test specimen requires this.

In the embodiment of FIG. 9, the longitudinal axes of the central element and the branch elements are no longer in one flat plane. The "plane" in "in plane bending" and "out of plane bending" now refers to the curved plane extending through the longitudinal axes of the central element and the branch elements. This means that in the in plane bending mode, the central element still vibrates in the direction indicated by arrow A in FIG. 9a, and in the out of plane bending mode in the direction indicated by arrow B in FIG. 9b. The branch elements 3,5 deflect accordingly.

This variant is also possible in combination with the test specimens as shown in FIG. 2 and FIG. 3. In those situations, the longitudinal axes 13,15 of the branch elements 3,5 extend under an angle relative to the longitudinal axis 12 of the central element and the longitudinal axes 13,15 of the branch elements 3,5 extend under an angle relative to each other. Also the other test specimens according to the invention can be modified this way.

FIG. 10 shows another variant of the test specimen 1 according to FIG. 1. FIG. 10a shows the test specimen 1 in front view, FIG. 10b shows the test specimen 1 in top view.

In the variant of FIG. 10, shores or stiffeners 10 are provided between the branch elements 3,5 and the central element 2. This changes to load distribution in the test specimen 1. Using this variant of the test specimen 1 can be useful if the actual structure also contains such shores or stiffeners.

Shores and/or stiffeners 10 as shown in FIG. 10 can also be applied in the other test specimens according to the invention.

Figure 11A:
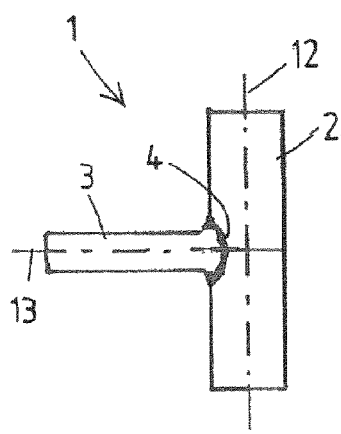
Figure 11B:
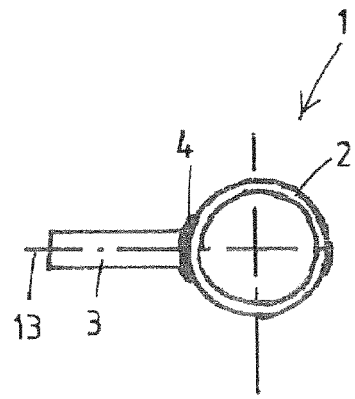

FIG. 11 shows another variant of the test specimen 1 according to FIG. 1. FIG. 11a shows the test specimen 1 in front view, FIG. 11b shows the test specimen 1 in top view.

The test specimen 1 of FIG. 11 is similar to the test specimen 1 of FIG. 1, only it has just one branch element 3.

As a result, the in plane bending resonance frequency and the out of plane bending frequency are farther apart than in the test specimen 1 of FIG. 1. Also the nodes in the branch element 3 for the in plane bending mode shape and the out of plane bending mode shape are farther apart. Therefore, for the test specimen 1 of FIG. 11, the weight distribution has to be optimized in order to obtain the desired values of the in plane bending resonance frequency and the out of plane bending frequency and position of the node on the branch element 3 for the in plane bending mode shape and the out of plane bending mode shape.

Figure 12A:
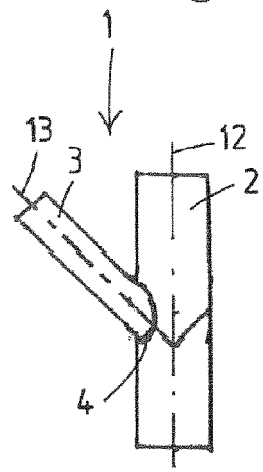
Figure 12B:
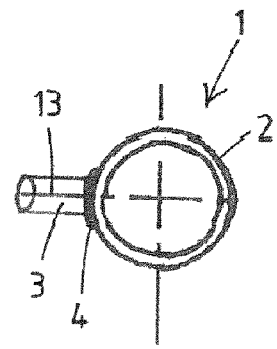

FIG. 12 shows a variant of the test specimen 1 according to FIG. 2. FIG. 12a shows the test specimen 1 in front view, FIG. 12b shows the test specimen 1 in top view.

The test specimen 1 of FIG. 12 is similar to the test specimen 1 of FIG. 2, only it has just one branch element 3. As a result, the in plane bending resonance frequency and the out of plane bending frequency are farther apart than in the test specimen 1 of FIG. 1. Also the nodes in the branch element 3 for the in plane bending mode shape and the out of plane bending mode shape are farther apart. Therefore, for the test specimen 1 of FIG. 11, the weight distribution has to be optimized in order to obtain the desired values of the in plane bending resonance frequency and the out of plane bending frequency and position of the node on the branch element 3 for the in plane bending mode shape and the out of plane bending mode shape.

Figure 13A:
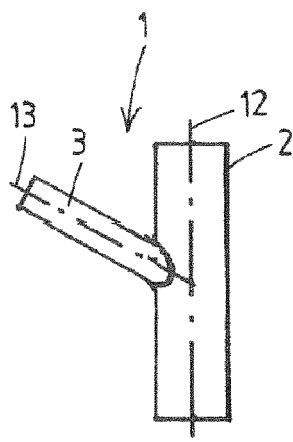
Figure 13B:
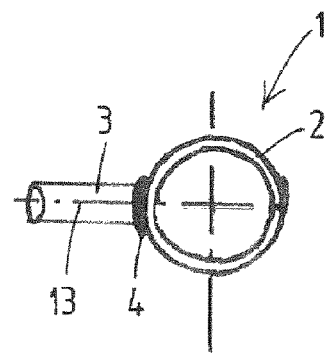

FIG. 13 shows a variant of the test specimen 1 according to FIG. 3. FIG. 13a shows the test specimen 1 in front view, FIG. 13b shows the test specimen 1 in top view.

The test specimen 1 of FIG. 13 is similar to the test specimen 1 of FIG. 3, only it has just one branch element 3. As a result, the in plane bending resonance frequency and the out of plane bending frequency are farther apart than in the test specimen 1 of FIG. 1. Also the nodes in the branch element 3 for the in plane bending mode shape and the out of plane bending mode shape are farther apart. Therefore, for the test specimen 1 of FIG. 11, the weight distribution has to be optimized in order to obtain the desired values of the in plane bending resonance frequency and the out of plane bending frequency and position of the node on the branch element 3 for the in plane bending mode shape and the out of plane bending mode shape.

Figures 14A, 14B:
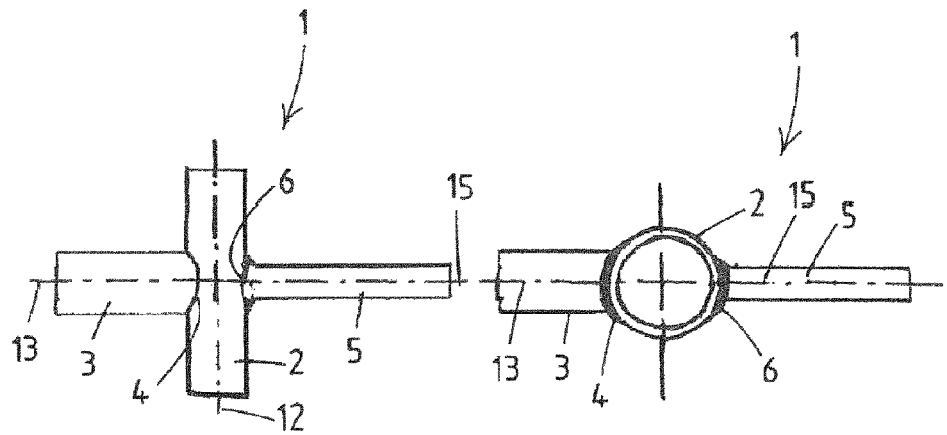

FIG. 14 shows another variant of the test specimen 1 according to FIG. 1. FIG. 14a shows the test specimen 1 in front view, FIG. 14b shows the test specimen 1 in top view.

In the embodiment, the first branch element 3 and the second branch element 5 have a different geometry. The first branch element 3 has a lager diameter than the second branch element 5 and the second branch element 5 is longer than the first branch element 3.

This different geometry of the two branch elements can also occur in the embodiments shown in FIGS. 2, 3, 8, 9 and 10.

Figures 15A, 15B:
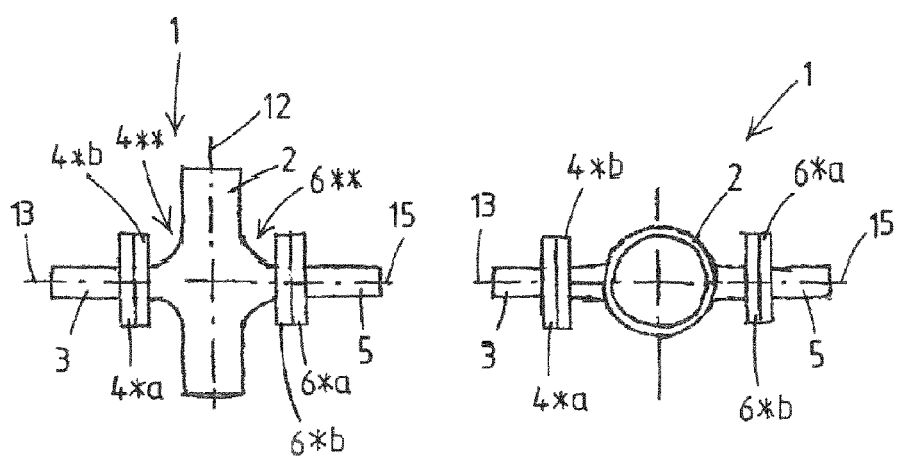

FIG. 15 shows another variant of the test specimen 1 according to FIG. 1. FIG. 15a shows the test specimen 1 in front view, FIG. 15b shows the test specimen 1 in top view.

In the embodiment of FIG. 15, the test specimen 1 has been provided with flanges 4*a,4*b and 6*a, 6*b to connect the first branch element 3 and the second branch element 5, respectively to the central element 2. The central element has two transition zones 4 and 6 that are present adjacent to the flanges 4*b and 6*b of the central element 2.

The flange 4*a of the central element 2 and the flange 4*b of the first element 3 are for example connected to each other by bolts and nuts, by a weld or by glue. The flange 6*a of the central element 2 and the flange 6*b of the second element 5 are also for example connected to each other by bolts and nuts, by a weld or by glue.

A joint with flanges can also occur in the embodiments of FIGS. 2, 3, 8, 9, 10, 11, 12, 13 and 14.

FIG. 16 shows another variant of the test specimen 1 according to FIG. 1. FIG. 16a shows the test specimen 1 in front view, FIG. 16b shows the test specimen 1 in top view.

In the embodiment of FIG. 16, the central element 2, the first branch element 3 and the second branch element 5 are made as a single part, for example by casting or as a single part from fiber reinforced resin. In this embodiment, the joint 4 is formed by the connection between the central element 2 and the first branch element 3. Joint 6 is formed by the connection between the central element 2 and the second branch element 5.

A joint of this type can also occur in the embodiments of FIGS. 2, 3, 8, 9, 10, 11, 12, 13 and 14.

FIG. 17 shows a further example of a test specimen 1 according to the invention. In this embodiment, two branch elements 3, 5 are present that both are provided with stiffeners in the form of stiffener plates 11.

In the embodiment of FIG. 17, the test specimen 1 comprises a central element 2, a first branch element 3 and a second branch element 5. The first branch element 3 and second branch element 5 extend coaxially with each other, both at an angle of 90° relative to the central element 2. However, the stiffener plates 11 as shown in this embodiment can also be used in embodiments that have a different geometry than the geometry shown in FIG. 17, for example in test specimens in which a different number of branch elements is present, in which the branch element or branch elements extend at a different angle from the central element and/or in which the branch elements do not extend coaxially with each other.

In the embodiment of FIG. 17, each branch element 3,5 is provided with two stiffener plates 11 on diametrically opposite sides of said branch element 3,5. The stiffener plates 11 are attached to each branch element 3, 5 between the joint 4, 6 that connects the respective branch element 3,5 to the central element 2 and the area in which the test specimen is engaged by the supports of the test rig, e.g. at or near the flanges 17.

In the embodiment of FIG. 17, the stiffener plates 11 extend in the plane of the out of plane bending mode. The stiffener plates 11 increase the stiffness of the test specimen, in particular the stiffness of the branch elements 3, 5 in the direction in which the deformation of the test specimen in the out of plane bending mode occurs. This shifts the resonance frequency of the out of plane bending mode upwards.

The joints between the central element 2 and the respective branch elements 3, 5 have different stress concentrations factors associated with them for the in plane bending mode on the one hand and the out of plane bending mode on the other. In this embodiment, the stress concentration factor that is associated with the in plane bending mode is lower than the stress concentration factor that is associated with the out of plane bending mode.

In the embodiment of FIG. 17, the testing frequency is preferably selected closer to the resonance frequency of the in plane bending mode, as this bending mode induces the lower stress concentrations in the joints 4,6 than the out of plane bending mode. This makes that the test specimen still receives the desired level of mechanical loads in the in plane bending mode, even though that bending mode is associated with lower stress concentrations.

The invention claimed is:

1. A combination of a test rig and a test specimen for performing a fatigue test of said test specimen,
   wherein the test specimen is non-axisymmetric and comprises:
   a central element, said central element having a longitudinal axis,
   a first branch element, said first branch element having a longitudinal axis that extends at an angle to the longitudinal axis of the central element, wherein the angle is other than 0° or 180°, and
   a joint connecting the first branch element to the central element,
   wherein the non-axisymmetric test specimen has a plurality of resonance frequencies with associated mode shapes, which plurality of resonance frequencies comprises an in-plane bending resonance frequency with an associated in-plane bending mode shape, and an out-of-plane bending resonance frequency with an associated out-of-plane bending mode shape, wherein the in-plane bending resonance frequency and the out-of-plane bending frequency are substantially the same,
   wherein the in-plane bending mode shape comprises a first node, which first node is located at the first branch element, and wherein the out-of-plane bending mode shape comprises a first node, which first node is located at the first branch element,
   wherein the first node of the in-plane bending mode shape and the first node of the out-of plane bending mode shape are substantially at the same position at the first branch element,
   and wherein the test rig comprises:
   a first support for supporting the test specimen, which first support supports the test specimen at or adjacent to the node of the in-plane bending mode shape and the out-of-plane bending mode shape, and
   an excitator for subjecting the test specimen to forced vibration at an excitation frequency.

2. The combination of the test rig and the test specimen according to claim 1,
   wherein the test specimen further comprises:
   a second branch element, said second branch element having a longitudinal axis that extends at an angle to the longitudinal axis of the central element, wherein the angle between the longitudinal axis of the second branch element and the longitudinal axis of the central element is other than 0° or 180°, and
   a joint connecting the second branch element to the central element,
   and wherein the test rig further comprises a second support for supporting the test specimen at the second branch element.

3. The combination of the test rig and the test specimen according to claim 2,
   wherein the in-plane bending mode shape further comprises a second node, which second node is located at the second branch element, and wherein the out-of-plane bending mode shape further comprises a second node, which second node is located at the second branch element,
   wherein the second node of the in-plane bending mode shape and the second node of the out-of-plane bending mode shape are substantially at the same position at the second branch element,
   wherein the second support of the test rig supports the second branch element at or adjacent to the second node of both the in-plane bending mode shape and the out-of-plane bending mode shape.

4. The combination of the test rig and the test specimen according to claim 1,
   wherein the joint between the first branch element and the central element is a weld or a threaded connection or a flange connection or a part of a cast structural element or a glued connection.

5. The combination of the test rig and the test specimen according to claim 1,
   wherein the central element and/or at least one branch element of the test specimen is tubular, or the central element and all branch elements are tubular.

6. The combination of the test rig and the test specimen according to claim 1,
   wherein in the test specimen, the angle between the longitudinal axis of the central element and the longitudinal axis of the first branch element is between 30° and 150°.

7. The combination of the test rig and the test specimen according to claim 2,
   wherein in the test specimen, the angle between the longitudinal axis of the first branch element and the longitudinal axis of the central element is substantially the same as the angle between the longitudinal axis of the second branch element and the longitudinal axis of the central element.

8. The combination of the test rig and the test specimen according to claim 2,
   wherein in the test specimen, the first branch element and the second branch element are coaxial with each other, and/or
   wherein the first branch element and the second branch element are on opposite sides of the central element, and/or
   wherein the first branch element and the second branch element are connected to the central element at the same level, optionally halfway between the ends of the central element, and/or
   wherein the longitudinal axis of the first branch element, the longitudinal axis of the second branch element and the longitudinal axis of the central element are in the same plane.

9. The combination of the test rig and the test specimen according to claim 1,
   wherein the test specimen comprises at least one cavity, which cavity is filled with a liquid or a gas, optionally a compressed gas, and/or which cavity is at least partly limited by at least one joint between the central element and a branch element.

10. The combination of the test rig and the test specimen according to claim 1,
    wherein the test specimen is provided with an additional test weight at the central element and/or at at least one branch element,
    wherein optionally the additional test weight is arranged non-coaxial with the at least one branch element.

11. The combination of the test rig and the test specimen according to claim 2,
    wherein the first branch element of the test specimen is provided with a first additional test weight and the second branch element of the test specimen is provided with a second additional test weight.

12. The combination of the test rig and the test specimen according to claim 1,
    wherein at least the first support of the test rig is moveable such that its position can be matched to the position of the first node of the in-plane bending mode shape and/or of the out-of-plane bending mode shape.

13. The combination of the test rig and the test specimen according to claim 1,
wherein the test specimen further comprises:
a second branch element, said second branch element having a longitudinal axis that extends at an angle to the longitudinal axis of the central element, wherein the angle between the longitudinal axis of the second branch element and the longitudinal axis of the central element is other than 0° or 180°,
a weld connecting the second branch element to the central element,
wherein the in-plane bending mode shape further comprises a second node, which second node is located at the second branch element, and wherein the out-of-plane bending mode shape further comprises a second node, which second node is located at the second branch element,
wherein the second node of the in-plane bending mode shape and the second node of the out-of-plane bending mode shape are substantially at the same position at the second branch element,
wherein the longitudinal axes of the central element, the first branch element and the second branch element are all in the same plane and the two branch elements are connected to the central element at the same level, and
wherein the angle between the longitudinal axis of the central element and the longitudinal axis of each branch element is between 30° and 150°,
and wherein the test rig further comprises a second support for supporting the test specimen at the second branch element, wherein the second support of the test rig supports the second branch element at or adjacent to the second node of both the in-plane bending mode shape and the out-of-plane bending mode shape.

14. The combination of the test rig and the test specimen according to claim 1,
wherein the first branch element is provided with a stiffener, which stiffener is attached to said first branch element between the joint connecting said first branch element to the central element and the location where the support of the test rig engages said first branch element.

15. A method for performing a fatigue test on a test specimen in a test rig,
wherein the test specimen is non-axisymmetric and comprises:
a central element, said central element having a longitudinal axis,
a first branch element, said first branch element having a longitudinal axis that extends at an angle to the longitudinal axis of the central element, wherein the angle is other than 0° or 180°, and
a joint connecting the first branch element to the central element,
wherein the non-axisymmetric test specimen has a plurality of resonance frequencies with associated mode shapes, which plurality of resonance frequencies comprises an in-plane bending resonance frequency with an associated in-plane bending mode shape, and an out-of-plane bending resonance frequency with an associated out-of-plane bending mode shape, wherein the in-plane bending resonance frequency and the out-of-plane bending frequency are substantially the same,
wherein the in-plane bending mode shape comprises a first node, which first node is located at the first branch element, and wherein the out-of-plane bending mode shape comprises a first node, which first node is located at the first branch element,
wherein the first node of the in-plane bending mode shape and the first node of the out-of-plane bending mode shape are substantially at the same position at the first branch element,
and wherein the test rig comprises:
a first support for supporting the test specimen, which first support supports the test specimen at or adjacent to the node of the in-plane bending mode shape and the out-of-plane bending mode shape, and
an excitator for subjecting the test specimen to forced vibration at an excitation frequency,
wherein the method comprises the following steps:
providing a combination of the test rig and the test specimen,
arranging the test specimen in the test rig, such that the first support of the test rig supports the first branch element at or adjacent to the first node of both the in-plane bending mode shape and the out-of-plane bending mode shape, and
subjecting the test specimen to forced vibration by the excitator at an excitation frequency that is close to the in-plane bending resonance frequency and the out-of-plane bending resonance frequency, thereby exciting the in-plane bending mode and the out-of-plane bending mode.

16. The method according to claim 15,
wherein the test specimen further comprises:
a second branch element, said second branch element having a longitudinal axis that extends at an angle to the longitudinal axis of the central element, wherein the angle between the longitudinal axis of the second branch element and the longitudinal axis of the central element is other than 0° or 180°, and
a joint connecting the second branch element to the central element,
wherein the in-plane bending mode shape further comprises a second node, which second node is located at the second branch element, and wherein the out-of-plane bending mode shape further comprises a second node, which second node is located at the second branch element,
wherein the second node of the in-plane bending mode shape and the second node of the out-of-plane bending mode shape are substantially at the same position at the second branch element,
wherein the test rig further comprises a second supporting the the test specimen at the second branch element,
wherein the second support of the test rig supports the second branch element at or adjacent to the second node of both the in-plane bending mode shape and the out-of-plane bending mode shape,
and wherein the method further comprises arranging the test specimen in the test rig such that the second support of the test rig supports the second branch element at or adjacent to the second node of both the in-plane bending mode shape and the out-of-plane bending mode shape.

17. The method according to claim 16, wherein at least the first support of the test rig is moveable such that its position can be matched to the position of the first node of the in-plane bending mode shape and/or of the out-of-plane bending mode shape,
and
wherein prior to or during the arranging of the test specimen on the test rig, the position of the first and/or second support of the test rig is adjusted.

18. The method according to claim 15, wherein the test specimen comprises at least one cavity, which cavity is filled with a liquid or a gas, and/or which cavity is at least partly limited by at least one joint between the central element and a branch element, and wherein the method further comprises the step of filling of said cavity of the test specimen with a liquid or a gas, optionally a compressed gas, and wherein pressure of the liquid or gas is measured during the test.

19. The method according to claim 15, wherein the first branch element is provided with a stiffener, which stiffener is attached to said first branch element between the joint connecting said first branch element to the central element and the location where the support of the test rig engages said first branch element, wherein excitation of the test specimen in the in-plane bending mode causes a first stress concentration in the joint and wherein excitation of the test specimen in the out-of-plane bending mode causes a second stress concentration in the joint, wherein a test frequency is selected closer to the resonance frequency associated with the bending mode that is associated with the lowest of the first stress concentration and the second stress concentration than to the resonance frequency associated with the bending mode that is associated with the highest of the first stress concentration and the second stress concentration.

20. A method for designing a fatigue test of a test specimen, in which fatigue test a combination of a test rig and test structure is used, wherein the test specimen is non-axisymmetric and comprises:

a central element, said central element having a longitudinal axis, a first branch element, said first branch element having a longitudinal axis that extends at an angle to the longitudinal axis of the central element, wherein the angle is other than 0° or 180°, and a joint connecting the first branch element to the central element, wherein the non-axisymmetric test specimen has a plurality of resonance frequencies with associated mode shapes, which plurality of resonance frequencies comprises an in-plane bending resonance frequency with an associated in-plane bending mode shape, and an out-of-plane bending resonance frequency with an associated out-of-plane bending mode shape, wherein the in-plane bending resonance frequency and the out-of-plane bending frequency are substantially the same, wherein the in-plane bending mode shape comprises a first node, which first node is located at the first branch element, and wherein the out-of-plane bending mode shape comprises a first node, which first node is located at the first branch element, wherein the first node of the in-plane bending mode shape and the first node of the out-of-plane bending mode shape are substantially at the same position at the first branch element, wherein the test rig comprises:

a first support for supporting the test specimen, which first support supports the test specimen at or adjacent to the node of the in-plane bending mode shape and the out-of-plane bending mode shape, and an excitator for subjecting the test specimen to forced vibration at an excitation frequency, wherein the performance of the fatigue test comprises the following steps:

providing a combination of the test rig and the test specimen, arranging the test specimen in the test rig, such that the first support of the test rig supports the first branch element at or adjacent to the first node of both the in-plane bending mode shape and the out-of-plane bending mode shape, and subjecting the test specimen to forced vibration by the excitator at an excitation frequency that is close to the in-plane bending resonance frequency and the out-of-plane bending resonance frequency, thereby exciting the in-plane bending mode and the out-of-plane bending mode, and wherein the method for designing the fatigue test comprises the following steps:

selecting a base geometry for the test specimen, including selecting the number of branch elements to be connected to the central element and the position and direction of these branch elements, selecting the shape of the central element and any branch elements, selecting the length and cross-sectional sizes of the central element and any branch elements, calculating the in-plane bending resonance frequency, the in-plane bending mode shape, the out-of-plane bending resonance frequency, the out-of-plane bending mode shape and optionally any further resonance frequencies that are close to the in-plane bending resonance frequency and/or out-of-plane bending resonance frequency, determining the difference between the in-plane bending resonance frequency and the out-of-plane bending resonance frequency, evaluating whether this difference between the in-plane bending resonance frequency and the out-of-plane bending resonance frequency is small enough to each other to be able to apply the method for performing a fatigue test according to claim 15, determining the difference in location of the node each branch element in the in-plane bending mode shape and the location of this node in the out-of-plane bending mode shape, optionally evaluating whether this difference in location of the node each branch element in the in-plane bending mode shape and the location of this node in the out-of-plane bending mode shape is small enough to each other to be able to apply the method for performing a fatigue test according to claim 15, and if the difference between the in-plane bending resonance frequency and the out-of-plane bending resonance frequency or if the calculated difference in location of the node each branch element in the in-plane bending mode shape and the location of this node in the out-of-plane bending mode shape is too large, adapting the weight distribution in the test specimen and/or the length and cross-sectional sizes of the central element and any branch elements and/or adapting the stiffness of a branch element and/or the central element in at least one direction by attaching a stiffener to said branch element and/or central element in order to shift the location of the nodes and/or the resonance frequencies.

21. A test specimen, wherein the test specimen is non-axisymmetric and comprises :

a central element, said central element having a longitudinal axis, a first branch element, said first branch element being made of metal and having a longitudinal axis that extends at an angle to the longitudinal axis of the central element, wherein the angle is other than 0° or 180°, and a joint connecting the first branch element to the central element, wherein the non-axisymmetric test specimen has a plurality of resonance frequencies with associated mode shapes, which plurality of resonance frequencies comprises an in-plane bending resonance frequency with an associated in plane bending mode shape, and an out-of-plane bending resonance frequency with an associated out-of-plane bending mode shape, wherein the in-plane bending mode shape comprises a first node, which first node is located at the first branch element, and wherein the out-of-plane bending mode shape comprises a first node, which first node is located at the first branch element, the first node of the in-plane bending mode shape and the first node of the out-of-plane bending mode shape being substantially at the same position at the first branch element, and wherein the test specimen is further provided with at least one support for a sensor, and/or wherein the test specimen is provided with an additional test weight at the central element and/or at at least one branch element, wherein optionally the additional test weight is arranged non-coaxial with the branch element.

22. The combination of the test rig and the test specimen according to claim 3, wherein the joint between the second branch element and the central element is a weld or a threaded connection or a flange connection or a part of a cast structural element or a glued connection.

23. The combination of the test rig and the test specimen according to claim 11, wherein the first additional test weight is different from the second additional test weight and/or wherein the location at which the first additional test weight is arranged at the first branch element is different from the location at which the second additional test weight is arranged at the second branch element.

* * * * *